US008293532B2

(12) United States Patent
Moynahan

(10) Patent No.: US 8,293,532 B2
(45) Date of Patent: Oct. 23, 2012

(54) METHOD AND APPARATUS FOR TISSUE TRANSFER

(75) Inventor: Tonya Lynne Strange Moynahan, Brownsburg, IN (US)

(73) Assignee: Dow AgroSciences, L.L.C., Indianapolis, MN (US)

( * ) Notice: Subject to any disclaimer, the term of this patent is extended or adjusted under 35 U.S.C. 154(b) by 29 days.

(21) Appl. No.: 12/724,965

(22) Filed: Mar. 16, 2010

(65) Prior Publication Data

US 2010/0248370 A1 Sep. 30, 2010

Related U.S. Application Data

(60) Provisional application No. 61/163,625, filed on Mar. 26, 2009.

(51) Int. Cl.
*C12N 5/02* (2006.01)
(52) U.S. Cl. ........................................................ 435/430
(58) Field of Classification Search .................. None
See application file for complete search history.

(56) References Cited

U.S. PATENT DOCUMENTS

| | | | |
|---|---|---|---|
| 4,170,861 A | 10/1979 | Snyder et al. | |
| 4,299,683 A | 11/1981 | Adorno et al. | |
| 4,318,884 A | 3/1982 | Suzuki | |
| 4,572,067 A | 2/1986 | Fischer | |
| 5,160,558 A | 11/1992 | Gardener | |
| 5,240,680 A | 8/1993 | Zuckermann et al. | |
| 5,324,482 A * | 6/1994 | Scaramella et al. | 422/526 |
| 6,137,860 A | 10/2000 | Ellegood et al. | |
| 6,600,423 B1 | 7/2003 | Rozier et al. | |
| 6,893,611 B1 | 5/2005 | Cohen et al. | |
| 6,945,129 B2 | 9/2005 | Escal | |
| 7,017,622 B2 | 3/2006 | Osborne et al. | |
| 7,105,338 B1 | 9/2006 | Holmes et al. | |
| 7,150,993 B2 | 12/2006 | Davis et al. | |
| 7,302,307 B1 | 11/2007 | Anderson et al. | |
| 2002/0051736 A1 | 5/2002 | Zucker | |
| 2002/0153098 A1 | 10/2002 | Kuroda et al. | |
| 2006/0029635 A1 | 2/2006 | Siebold et al. | |
| 2006/0212056 A1* | 9/2006 | Salvadori et al. | 606/167 |
| 2007/0281347 A1 | 12/2007 | Boeckeler et al. | |
| 2008/0029133 A1 | 2/2008 | Kunkle | |

FOREIGN PATENT DOCUMENTS

| | | |
|---|---|---|
| CN | 1851589 | 10/2006 |
| DE | 3046016 | 9/1981 |
| DE | 19925658 | 12/2000 |
| JP | 6225753 | 8/1994 |
| KR | 20030022435 | 3/2003 |
| KR | 20030022436 | 3/2003 |
| KR | 20060061525 | 8/2006 |
| KR | 20070000583 | 3/2007 |
| RU | 2153101 | 7/2000 |
| WO | WO 9312427 | 6/1993 |
| WO | WO 9949320 | 9/1999 |
| WO | WO 0010761 | 3/2000 |
| WO | WO 0103741 | 1/2001 |
| WO | WO 0196881 | 12/2001 |
| WO | WO 0216687 | 2/2002 |
| WO | WO 2004/050038 | 6/2004 |
| WO | WO 2006/056920 | 6/2006 |
| WO | WO 2007/027635 | 3/2007 |
| WO | WO 2007/140531 | 12/2007 |

OTHER PUBLICATIONS

Establishement of a single-step hybridoma cloning protocol using an automated cell transfer system:comparason with limiting dilution. Wewetzer et al. Journal of Immunological Methods 179 (1995) 71-76.*
Mineo Plant Tissue Culture Techniques. pp. 151-174 in Tested studies for laboratory teaching vol. 11 (C. A. Goldman Editor). Proceedings of the Eleventh Workshop/Conference of the Association for Biology Laboratory Education 195 pages.*
Hull, Case for electronic preheating in automated transfer molding of thermosetting plastics, Hull Corp., Hatboro, PA, Modern Plastics (1967) (abstract).
Klie, Sulfer determination in coal by 14 MeV neutron activation analysis, Guelph-Waterloo Cent. Grad. Work Chem., Univ. Waterloo, Waterloo, ON, Can., Journal of Radioanalytical Chemistry (299-309) (1982) (abstract).
Riabkova, Physiological and hygienic evaluation of work at the automated transfer lines of the roofing paper plant, Gigiena truda I professional'nye zabolevaniia (46-7) (1984) (abstract).
Haky, Automated data processing for chromatographic assay method validations, Chem. Dep., Warner-Lambert/Parke-Davis Pharm. Res., Ann Arbor, MI, Journal of Chromatographic Science (364-9) (1985) (abstract).
Barth, Modern rubber molding manufacture, Fed. Rep. Ger. Gummi, Fasem, Kunststoffe (14-16) (1987) (abstract).
Nishine, Development and application of a new apparatus for two-dimensional electrophoresis involving a transfer robot, Bio-Tech. Instrum. Dep., Shimadzu Corp., Kyoto, Japan (247-51) (1991) (abstract).
Nishine,Design and applications of an automated apparatus for two-dimensional electrophoresis, Shimadzu model TEP-1, Biotechnol. Instrum. Dep., Shimadzu Corp., Kyoto, Japan, Analytical Sciences (285-8) (1991) (abstract).
Biederbick, Adur—automatic decanting of low temperature liquefied gases, Gas Aktuell (26-9) (1991) (abstract).

(Continued)

*Primary Examiner* — Annette Para
(74) *Attorney, Agent, or Firm* — Ronald S. Maciak; Faegre Baker Daniels LLP

(57) ABSTRACT

A handheld tool is disclosed which may be used to transfer a plurality of plant tissue explants from a first container to a second container. The handheld tool may include a disposable tip member which couples the plurality of plant tissue explants through use of negative pressure. An automated system which transfers a plurality of plant tissue explants from a first container to a second container is also disclosed. The automated system may include a first presentment system which moves the first container to a region, a second presentment system which moves the second container to the region, and a robot system that transfers the plurality of plant tissue explants from the first container to the second container.

13 Claims, 11 Drawing Sheets

OTHER PUBLICATIONS

Nokihara, Applications of an automated apparatus for two-dimensional electrophoresis, Model TEP-1, for microsequence analysis of proteins, Tokyo University of Agriculture and Technology, Japan Electrophoresis (1992) (abstract).

Piqueras, Data interface between a radiology information system and a computed radiography system using a personal computer and standard software, Department of Pediatric Radiology, Hospital Materno-Infantil Vall d'Hebron, Autonomous University of Barcelona, Spain, AJR American journal of roentgenology (1313-5) (1993) (abstract).

Fischler, Effects of automated transfer coalescing on production physics, Fermi National Accelerator Laboratory, Batavia, IL, Nuclear Physics B, Proceedings Supplements (823-5) (1994) (abstract).

Akiba, Application to plutonium and uranium in safeguards, Power Reactor Nuclear Fuel Development Corp., Japan, Nippon Aisotopu, Hoshasen Sogo Kaigi Hobunshu (1994) (abstract).

Wewetzer, Establishment of a single-step hybridoma cloning protocol using an automated cell transfer system: comparison with limiting dilution, Switzerland Journal of immunological methods (71-6) (1995) (abstract).

Koenig, Printing materials for automated transfer of ceramic decorations, Foprtschrittsberichte der Deutschen Keramischen Gesellschaft (25-33) (1995) (abstract).

Mondello, Italian Citrus petitgrain oils. Part 1. Composition of bitter orange petitgrain oil. Fac. Farm., Univ. Messina, Messina, Italy, Journal of Essential Oil Research (597-609) (1996) (abstract).

Banerji, Application of microalloyed forgings for heavy-duty diesel-engine connecting rods and other components, Fundamentals and Applications of Microalloying Forging Steels, Proceedings of a Symposium, Golden, CO (375-389) (1996) (abstract).

Michaelis, Columbus Orbital Facility and Automated Transfer Vehicle: a challenge for agency & industry, Daimler Benz Aerospace AG, Space Infrastructure Division, Acta astronautica (369-77) (1997) (abstract).

Gallier, 200-N Newton biopropellant thruster development, Groupe Petite Propulstion at Equipments Societe Europeenne de Propulsion, Moissy Cramayel, Fr., European Space Agency, [Special Publication] (425-428) (1997) (abstract).

Zats, Techniques for measuring in vitro release from semisolids, Rutgers College of Pharmacy, Piscataway, NJ, Dissolution Technologies (3, 6-13, 17) (1998) (abstract).

Krischnamurthy, Bacterial typing and identification by mass spectrometry, US Army Edgewood RDE Center, Aberdeen Proving Ground, MD, Book of Abstracts, 216th ACS National Meeting, Boston, Aug. 23-27, 1998 (abstract).

Yefimov, Transfer of SDS-proteins from gel electrophoretic zones into mass spectrometry, using electroelution of the band into buffer without sectioning of the gel, Laboratory of Cellular and Molecular Biophysics, Section on Macromolecular Analysis, National Institutes of Health, Bethesda, MD., Journal of Biochemical and Biophysical Methods (65-78) (2000) (abstract).

Schultz, Integrating digital teaching-file systems with off-the-shelf presentation software to facilitate speaker-led conferences, Department of Radiology, Massachusetts General Hospital, Boston, MA, Journal of digital imaging: the official journal of the Society for Computer Applications in Radiology (98-101) (2001) (abstract).

Ivanetich, Automated transfer of DNA sequencing files, Biomolecular Resource Center and Department of Pharmaceutical Chemistry, University of California, San Francisco, San Francisco, CA, American Biotechnology Laboratory (32, 34) (2001) (abstract).

Bolender, EAC trains its first international astronaut class, Astronaut Training Division, European Astronaut Centre (EAC), Cologne, Germany, ESA bulletin, Bulletin ASE, European Space Agency (50-5) (2002) (abstract).

Lindh, Internet based clinical trial protocols—as applied to a study of warfarin pharmacogenitcs, Division of Clinical Pharmacology, Karolinksa University Hospital Huddinge, Stockholm, Sweden, British journal of clinical pharmacology (482-7) (2004) (abstract).

Messerschmid, The European Astronaut Centre prepares for International Space Station operations, European Space Agency, Directorate of Manned Spaceflight and Microgravity, European Astronaut Centre, Cologne, Germany, Acta astronautica (527-39) (2004) (abstract).

Flanagan, Ontology for genome comparison and genomic rearrangements, School of Computing Science, University of Newcastle, Tyne, UK, Comparative and Functional Genomics (537-544) (2004) (abstract).

Tulock, Microfluidic Separation and Gateable Fraction Collection for Mass-Limited Samples, Department of Chemistry, Department of Mechanical and Industrial Engineering and Beckman Institute for Advanced Science and Technology, University of Illinois at Urbana-Champaign, Urbana, IL, Analytical Chemistry (6419-6425) (2004) (abstract).

Stuffler, The flight experiment ANITA—a high performance air analyser for manned space cabins, Kayser-Threde GmbH, Munich, Germany, Act Astronautica (573-579) (2004) (abstract).

Ohana et al., CATS: a Cryogenic Automated Transfer System installed on the beamline FIP at ESRF, Laboratoire de Cristallographie et Cristallogenese des Proteines (LCCP), Institute de Biologie Structurale J.-P. Ebel CEA-CNRS, Grenoble, Fr. Journal of Applied Crystallography (72-77) (2004) (abstract).

Winter, Foraging in a complex naturalistic environment: capacity of spatial working memory in flower bats, Department of Biology, University of Munich, The Journal of experimental biology (2005) (abstract).

Sclafani, Automated transfer of whole blood from closed vacutainers to prevent exposure to bioterrorism agents and other bloodborne pathogens, Emergency Response and Air Toxicants, Battelle/CDC, Atlanta, GA, Abstracts of Papers, 229th ACS National Meeting, San Diego, CA, Mar. 13-17, 2005 (abstract).

Tolk et al., Requirements for automated transfer of operator declarations, Annual Meeting Proceedings of the Institute of Nuclear Materials Management Institute of Nuclear Materials Management (2006)(abstract).

Pankop, Migration of thruster plume erosion of international space station solar array coatings, The Boeing Company, Houston, TX, Journal of Spacecraft and Rockets (545-550) (2006) (abstract).

VacuBoy, Scientific Visions, Inc. (2 pgs.) (available at least by Mar. 25, 2009).

MEDIAJET—Petri Dish Filler, IBS Integra Biosciences (4 pgs.) (available at least by Mar. 25, 2009).

MEDIAJET vario—The most versatile Petri dish filler available, IBS Integra Biosciences (2 pgs.) (available at least by Mar. 25, 2009).

Automatic Seeder, Dow AgroSciences LLC (1 pg.) (available at least by Mar. 25, 2009).

* cited by examiner

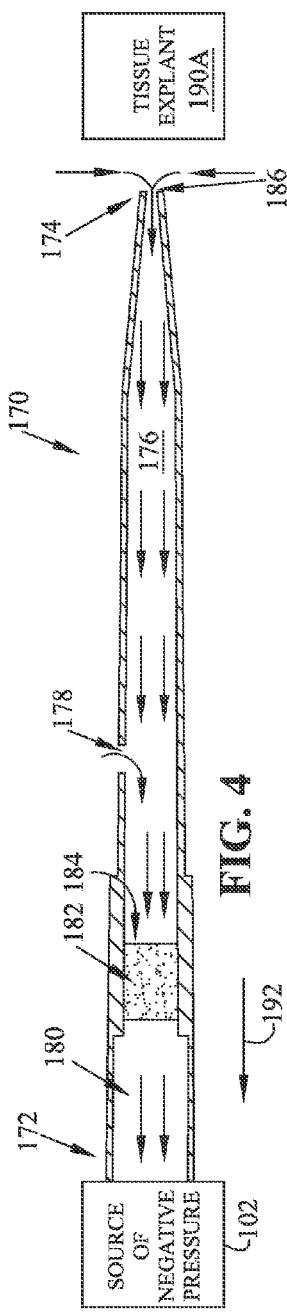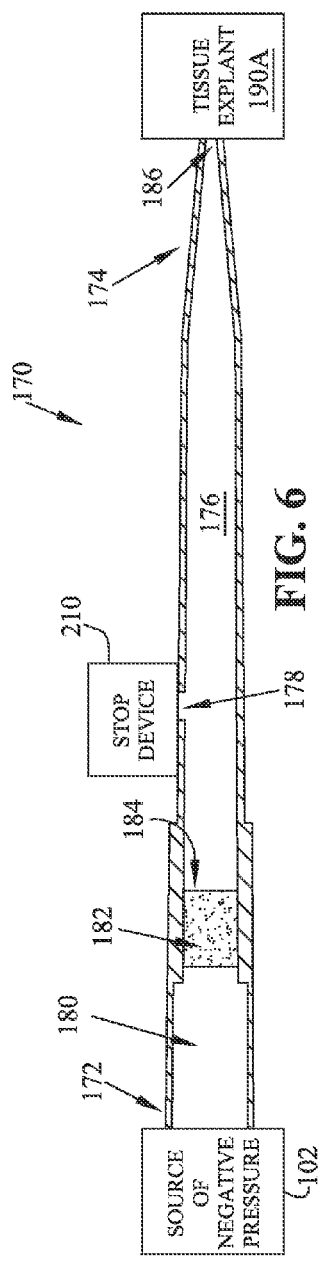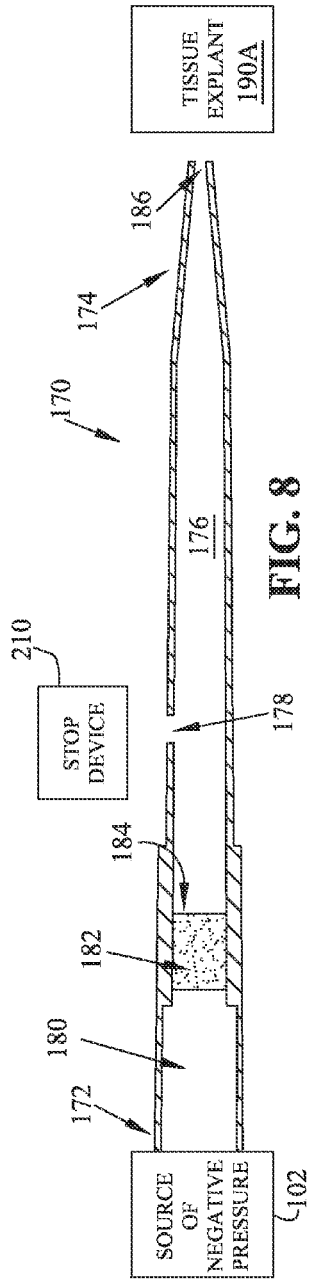

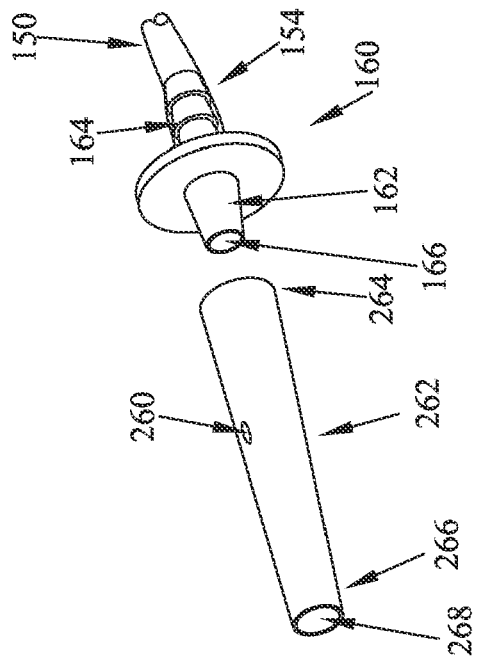
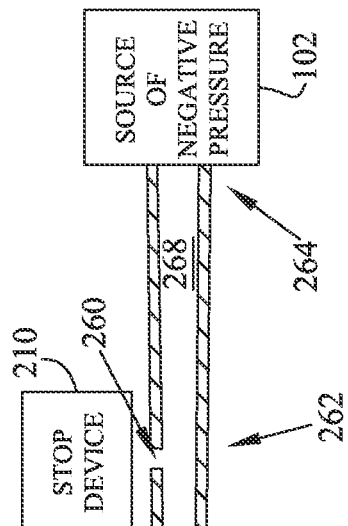
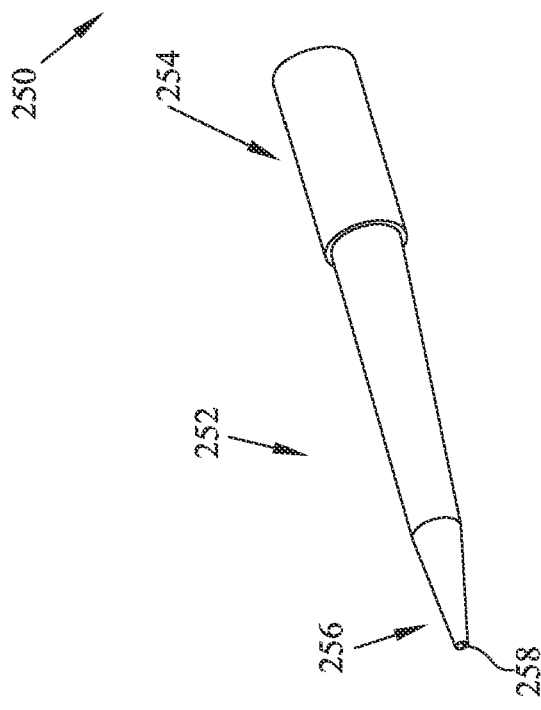
FIG. 10
FIG. 11

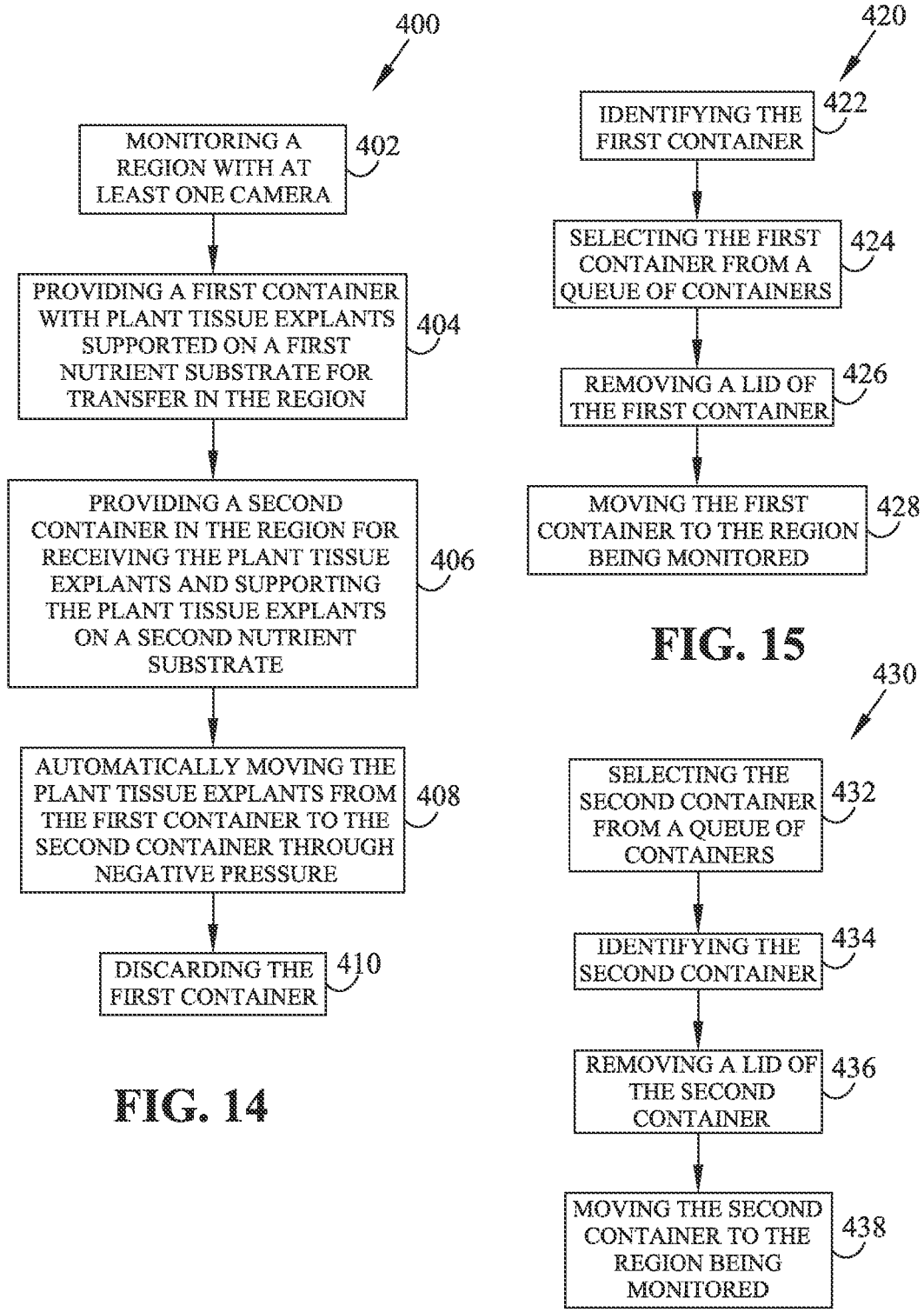

METHOD AND APPARATUS FOR TISSUE TRANSFER

CROSS REFERENCE TO RELATED APPLICATION

This application claims the benefit of U.S. Provisional Patent Application Ser. No. 61/163,625, filed Mar. 26, 2009, titled "METHOD AND APPARATUS FOR TISSUE TRANSFER", the disclosure of which is expressly incorporated by reference herein.

FIELD

The present invention relates to methods and apparatus for handling plant tissue cultures and in particular to methods and apparatus for handling the transfer of plant tissue culture explants.

BACKGROUND

Many different types of plant tissues are used in a research laboratory setting. In one example, plant tissue is grown outside of an intact plant as plant tissue cultures. This plant tissue is grown, maintained or otherwise cultured in an aseptic environment having a nutrient medium supporting the plant tissue. The plant tissue is often referred to in the art as plant tissue explants. One example of a plant tissue explant would be canola hypocotyl segments cut from germinated seeds.

The claimed methods and apparatus are particularly useful for manipulating plant tissue explants in preparation for recombinant DNA procedures and for handling explants and callus resulting from recombinant DNA techniques. These techniques are used to introduce novel transgenic events into plant cells to produce fertile plants bearing useful phenotypes such as herbicide tolerance and insect resistance.

Typically these plant tissue explants are matured in containers having solid or semi-solid nutrient medium and observed by trained professionals to determine the usefulness of a given plant tissue explant. By way of example, a plant tissue explant may be observed or assayed to identify those plant tissue explants that have advantageous characteristics or traits introduced by recombinant DNA technology.

Often several plant tissue explants are arranged in a container of solid or semi-solid nutrient substrate supporting the tissue explants. The substrate provides nutrients for the cells within the tissue and is generally comprised of a mixture of inorganic salts, vitamins, a carbon source such as sucrose, and plant growth regulators or hormones. The plant tissue explants change over time and are observed periodically by a trained professional. Several times during the observation period, the tissue explants must be transferred to a different substrate in order to assure adequate nutrient provision to the tissue explants.

In one example, maize embryos are stored in containers in a room having a temperature of about 28° C., about 30% humidity, and generally dark for about a one month period of time. During that one month period of time, the maize tissue pieces must be transferred to different containers with a different substrate to provide adequate nutrients to the tissue pieces. In an example, the maize tissue pieces are transferred once a week. In one example, about 50 individual maize tissue explants are provided in each of 100 containers.

In another example, canola tissue pieces are stored in containers in a room having a temperature of about 22-23° C. and generally dark for about 8 hours a day and light for 16 hours a day over about five to six weeks. During that five to six week period of time, the canola tissue pieces must be transferred to different containers with a different substrate to provide adequate nutrients to the tissue pieces. In an example, the canola tissue pieces are transferred every week or two weeks. In one example, about 20 to about 50 individual canola tissue pieces are provided in each of 40 containers. In one example, about 3 to about 5 mm canola segments are cut from germinated seeds and placed into containers each having the nutrient medium. In one experiment from about 1000 to about 2000 canola segments are provided (about 20 to about 100 containers) are provided. These 1000 to 2000 segments need to be transferred every week or two. Generally up until the fifth transfer, all of the 1000 to 2000 segments are to be transferred.

In a further example, cotton tissue explants are stored in containers in a room having a temperature of about 28° C. and generally dark for about 8 hours a day and in indirect lighting for 16 hours a day over about three months. During that three month period of time, the cotton tissue explants must be transferred to different containers with a different substrate to provide adequate nutrients to the tissue explants. In an example, the cotton tissue explants are transferred every four weeks. In one example, about 5 individual cotton tissue explants are provided in each of 300 containers.

Traditionally, plant tissue explants of a given crop have been transferred manually by a trained professional from a first container to a second container with forceps in an aseptic environment. The trained professional would place an individual tissue piece between the tongs of the forceps, squeeze the tongs together, pick up the individual tissue explant, and release the pressure on the tongs of the forceps when the tissue piece is located correctly relative to the second container. A professional may transfer up to about 3,000 tissue explants this way during a given eight hour work day. This process results in fatigue for the trained professional over time and potentially an increase in the risk of injury to the trained professional.

In addition, the transfer of tissue explants from the first container to the second container is performed in an aseptic environment. Traditionally, the transfer is performed in a laminar flow hood, such as the EDGEGUARD® brand laminar flow hood available from The Baker Company located in Sandford, Me. In addition, the forceps used for transferring the tissue explants must be sterilized between container transfers of a given set of tissue explants. This prevents cross contamination from one container transfer run (a first set of tissue explants from a first container to a second container) and a subsequent container transfer run (a second set of tissue explants from a third container to a fourth container). One method used to sterilize the forceps is to submerge the tip of the forceps in EtOH and pass the tongs of the forceps through an open flame. This creates a risk that the ethanol might ignite resulting in a contamination of the environment. Further, the hood in which the transfer was being performed may need to be serviced, such as the replacement of the HEPA filters in the hood. This takes the transfer station out of operation for a period of time.

SUMMARY

In an exemplary embodiment of the present disclosure, apparatus are provided which reduce the ergonomic injury risk and may increase productivity and capacity. Further, the apparatus may reduce the risk of contamination.

In another exemplary embodiment of the present disclosure, a method of transferring plant tissue explants from a first container having a first nutrient medium substrate adapted to provide nutrients to the plant tissue explants to a second container having a second nutrient medium substrate adapted to provide nutrients to the plant tissue explants is provided. The method comprising the steps of: (a) coupling a first plant tissue explant to a handheld tool, the handheld tool coupling the first plant tissue explant through a negative pressure present in an interior of the handheld tool; (b) generally separating the first plant tissue explant from the first nutrient medium substrate adapted to provide nutrients to the first plant tissue explant and from the first container; (c) locating the first plant tissue explant relative to the second nutrient medium substrate adapted to provide nutrients to the first plant tissue explant of the second container; and (d) uncoupling the first plant tissue explant from the handheld tool. In an example thereof, the handheld tool includes a fluid conduit having a first end and a second end. The second end of the fluid conduit being in fluid communication with the first end of the fluid conduit and the fluid conduit having at least one vent passage positioned between the first end of the fluid conduit and the second end of the fluid conduit. The vent passage being in fluid communication with the first end of the fluid conduit and the second end of the fluid conduit and to the surrounding environment. The vent passage being blocked from fluid communication with the surrounding environment during steps (a) through (c) with a stop device and the vent passage being in fluid communication with the surrounding environment during step (d). In a variation thereof, the stop device is one of an operator's finger and a device supported by the operator's finger. In another variation, the fluid conduit is an assembly and includes at least a first portion and a second portion, both the first portion and the second portion having a respective interior in fluid communication with the first end of the handheld tool and the second end of the handheld tool when the first portion and the second portion are assembled. In addition, the method further comprises the steps of: (e) providing a plurality of first portions of the handheld tool; (f) assembling a first one of the plurality of first portions of the handheld tool to the second portion of the handheld tool; (g) performing steps (a) through (d) for all of the plant tissue explants in the first container selected for transfer to the second container; (h) separating the first one of the plurality of first portions of the handheld tool from the second portion of the handheld tool; (i) obtaining a third container including another plurality of plant tissue explants for transfer to a fourth container; (j) assembling a second one of the plurality of first portions of the handheld tool to the second portion of the handheld tool; and (k) performing steps (a) through (d) for all of the plant tissue explants in the third container selected for transfer to the fourth container. In a refinement thereof, the plurality of first portions are a plurality of pipette tips. In a further refinement thereof, the plurality of pipette tips are stored generally vertical in a pipette tip box with a tip portion lower than a coupling portion and the step of assembling a first one of the plurality of first portions of the handheld tool to the second portion of the handheld tool includes the step inserting a portion of the second portion of the handheld tool into the coupling portion of a first pipette tip of the plurality of pipette tips while the first pipette tip is stored in the pipette tip box. In another example, the steps (a) through (d) are performed in an aseptic environment. In a variation thereof, steps (a) through (d) are performed in a laminar flow hood. In yet another example, the step of uncoupling the first plant tissue explant from the handheld tool includes the step of reducing the negative pressure in the handheld tool by opening a vent passage of the handheld tool.

In yet another exemplary embodiment of the present disclosure, a system coupled to a negative pressure source for use transferring plant tissue explants from a first container having a first nutrient medium substrate adapted to provide nutrients to the tissue explants to a second container having a second nutrient medium substrate adapted to provide nutrients to the plant tissue explants is provided. The system comprising a flexible fluid conduit having a first end adapted to be coupled to the negative pressure source and a second end which is in fluid communication with the first end through an interior of the flexible fluid conduit; a handheld, pen shaped instrument coupled to the second end of the flexible conduit, the handheld pen shaped instrument having an interior in fluid communication with the interior of the flexible fluid conduit; and a tip member removably coupled to the handheld pen shaped instrument. The tip member having an interior in fluid communication with the interior of the handheld pen shaped instrument and a first end having an opening in fluid communication with the interior of the tip member. The opening of the first end of the tip member being smaller than the plant tissue explants to prevent the plant tissue explants from entering the interior of the tip member when a negative pressure is present in the interior of the flexible fluid conduit, the handheld, pen-shaped instrument, and the tip member. In an example thereof, the handheld pen shaped instrument includes at least one vent passage along an exterior of the handheld pen shaped instrument and in fluid communication with the surrounding environment and the interior the handheld pen shaped instrument. When the vent passage is not in fluid communication with the surrounding environment, the negative pressure in the tip member is increased compared to when the vent passage is in fluid communication with the surrounding environment. In another example, the tip member is a pipette tip. In yet another example, the system further comprises a filter positioned between the first end of the flexible fluid conduit and the first end of the tip member. In a refinement thereof, the flexible fluid conduit is divided into a first portion and a second portion. The filter being housed in a housing which is interposed between the first portion and the second portion.

In still another exemplary embodiment of the present disclosure, a system coupled to a negative pressure source for use transferring plant tissue explants from a first container having a first nutrient medium substrate adapted to provide nutrients to the tissue explants to a second container having a second nutrient medium substrate adapted to provide nutrients to the plant tissue explants is provided. The system comprising a flexible fluid conduit having a first end adapted to be coupled to the negative pressure source and a second end which is in fluid communication with the first end through an interior of the flexible fluid conduit; and a tip member removably coupled to the flexible fluid conduit. The tip member having an interior in fluid communication with the interior of the flexible fluid conduit and a first end having an opening in fluid communication with the interior of the tip member. The opening of the first end of the tip member being smaller than the plant tissue explants to prevent the plant tissue explants from entering the interior of the tip member when a negative pressure is present in the interior of the flexible fluid conduit and the tip member. The tip member further includes at least one vent passage along an exterior of the tip member and in fluid communication with the surrounding environment and the interior the tip member. When the vent passage is not in fluid communication with the surrounding environment, the negative pressure in the tip member is increased compared to when the vent passage is in fluid communication with the surrounding environment. In an example thereof, the tip member is a pipette tip. In another example thereof, the system further comprises a filter positioned between the first end of the flexible fluid conduit and the first end of the tip member. In a variation thereof, the flexible fluid conduit is divided into a first portion and a second portion. The filter being housed in a housing which is interposed between the first portion and the second portion.

In yet still another exemplary embodiment of the present disclosure, a system coupled to a negative pressure source for use transferring a plurality of plant tissue explants from a first container having a first nutrient medium substrate adapted to provide nutrients to the tissue explants to a second container having a second nutrient medium substrate adapted to provide nutrients to the plant tissue explants is provided. The system comprising a robot system supporting a fluid conduit having an interior which is in fluid communication with the negative pressure source; at least one camera positioned to monitor a region including the first container and the second container; and a controller operatively coupled to the at least one camera and the robot system. The controller based on input from the at least one camera (a) moves the robot system to couple a first tissue explant of the plurality of plant tissue explants in the first container to the fluid conduit through negative pressure in the interior of the fluid conduit, (b) moves the robot system such that the first tissue explant is proximate the second nutrient medium of the second container; and (c) uncouples the first tissue explant from the fluid conduit such that the first tissue explant is left in the second container. In an example thereof, the controller repeats steps (a) through (c) for each of the plurality of plant tissue explants in the first container. In a variation thereof, each of the plurality of plant tissue explants are placed in the second container to form a predefined pattern. In another example, the system further comprises an identification system operatively coupled to the controller. The identification system including a reader which determines an identification of the first container and a marker which provides identifying indicia on the second container. In yet another example, the system further comprises a first presentment system which places the first container in the region and a second presentment system which places the second container in the region. In a variation thereof, the first presentment system removes the first container from a first queue of containers for transfer and places the first container in a queue of waste containers subsequent to a completion of the transfer of plant tissue from the first container to the second container. In a refinement thereof, the first presentment system is operatively coupled to the controller. The controller providing instructions to the first presentment system regarding the movement of the first container. In a further refinement thereof, the first presentment system includes a turntable which transports the first container from the first queue of containers for transfer to the region and from the region to the queue of waste containers. In yet another refinement, the second presentment system removes the second container from a second queue of containers for transfer and places the second container in a third queue of containers subsequent to a completion of the transfer of plant tissue from the first container to the second container. In a further refinement, the second presentment system is operatively coupled to the controller. The controller providing instructions to the second presentment system regarding the movement of the second container. In still a further refinement, the second presentment system includes a turntable which transports the second container from the second queue of containers for transfer to the region and from the region to the third queue of containers. In yet another example, the fluid conduit includes a removable tip member which interfaces with the plurality of tissue portions. In a variation thereof, the controller prior to steps (a) through (c) selects the removable tip member from a queue of removable tip members and subsequent to completion of steps (a) through (c) discards the removable tip member and selects a second removable tip member from the queue of removable tip members.

In yet still another exemplary embodiment of the present disclosure, a method of transferring plant tissue explants is provided. The method comprising the steps of: (a) monitoring a region with at least one camera; (b) providing a first container with a plurality of plant tissue explants supported on a first nutrient substrate for transfer in the monitored region; (c) providing a second container in the monitored region for receiving the plurality of plant tissue explants and supporting the plurality of plant tissue explants on a second nutrient substrate; and (d) automatically transferring the plant tissue explants from the first container to the second container through negative pressure applied by a robot system. In an example thereof, the robot system includes a fluid conduit in fluid communication with a source of negative pressure and the step of automatically transferring the plant tissue explants from the first container to the second container through negative pressure applied by a robot system includes the steps of: selecting a tip member from a queue of tip members; coupling the tip member to the robot system such that a first end of the tip member is in fluid communication with the fluid conduit; for each plant tissue explant in the first container: locating the respective plant tissue explant in the first container; positioning the first end of the tip member proximate the respective plant tissue explant; coupling the respective plant tissue explant to the first end of the tip member due to the first end of the tip member being in fluid communication with the source of negative pressure through a fluid conduit of the tip member; moving the tip member and the respective plant tissue explant to a predefined location relative to the second container; and uncoupling the respective plant tissue explant from the tip member by changing the pressure in the fluid conduit of the tip member; and uncoupling the tip member from the robot system and discarding the tip member. In an example thereof, the step of providing a first container with a plurality of plant tissue explants supported on a first nutrient substrate for transfer in the monitored region includes the steps of: identifying the first container; selecting the first container from a first queue of containers; removing a lid of the first container; and moving the first container to the region being monitored. In another example thereof, the step of providing a second container in the monitored region for receiving the plurality of plant tissue explants and supporting the plurality of plant tissue explants on a second nutrient substrate includes the steps of: selecting the second container from a second queue of containers; identifying the second container; removing a lid of the second container; and moving the second container to the region being monitored.

The above mentioned and other features of the invention, and the manner of attaining them, will become more apparent and the invention itself will be better understood by reference to the following description of embodiments of the invention taken in conjunction with the accompanying drawings.

BRIEF DESCRIPTION OF THE DRAWINGS

FIG. 4 illustrates a sectional view of the tip member of FIG. 3 along lines 4-4 and illustrating air flow through an interior of the tip member;

FIG. 6 illustrates the sectional view of FIG. 4 with a stop device blocking a vent passage of the tip member such that the first tissue explant is coupled to an end of the tip member;

FIG. 8 illustrates the sectional view of FIG. 4 with a stop device spaced apart from the vent passage of the tip member such that the first tissue explant is uncoupled from an end of the tip member;

FIG. 10 illustrates a portion of another handheld tool for use in transferring plant tissue explants in an aseptic environment, the handheld tool including a pen-shaped instrument having a vent passage and a tip member which is coupled to the pen-shaped instrument;

FIG. 11 illustrates the tip member and pen-shaped instrument of the handheld tool of FIG. 10;

FIG. 14 illustrates a representative method of using an automatic transfer system for transferring plant tissue explants from a first container to a second container;

FIG. 15 illustrates a representative method of providing a first container in a monitored region, the first container including a plurality of plant tissue explants for transfer to a second container.

FIG. 16 illustrates a representative method of providing a second container in the monitored region, the second container receiving the plurality of plant tissue explants transferred from the first container.

Corresponding reference characters indicate corresponding parts throughout the several views.

DETAILED DESCRIPTION OF THE DRAWINGS

The embodiments disclosed below are not intended to be exhaustive or to limit the invention to the precise forms disclosed in the following detailed description. Rather, the embodiments are chosen and described so that others skilled in the art may utilize their teachings. While the present disclosure is primarily directed to the transfer of crop tissue explants within a sterile environment, it should be understood that the features disclosed herein may have application to the transfer of other types of tissue or objects.

The term 'plant tissue culture explants' also be referred to as "plant tissue explants' or "plant tissue cultures' refer to any plant tissue growing or being maintained on a medium which consists of cells in protoplasmic continuity. Often these explants are multi-cellular consisting of morphologically complex structures. Plant tissue culture explants can include single cells or protoplasts, cell clusters, callus pieces, embryo-like structures, embryos, ovules, ovaries, anthers, microspores, pollen grains, hypocotyls, cotyledons, leaf segments, stem pieces, roots and seeds. Exemplary plant tissue culture explants include maize and cotton embryos, canola hypocotyls, cotton ovules, soybean cotyledons, tobacco leaf segments and rice callus pieces.

Figure 1:
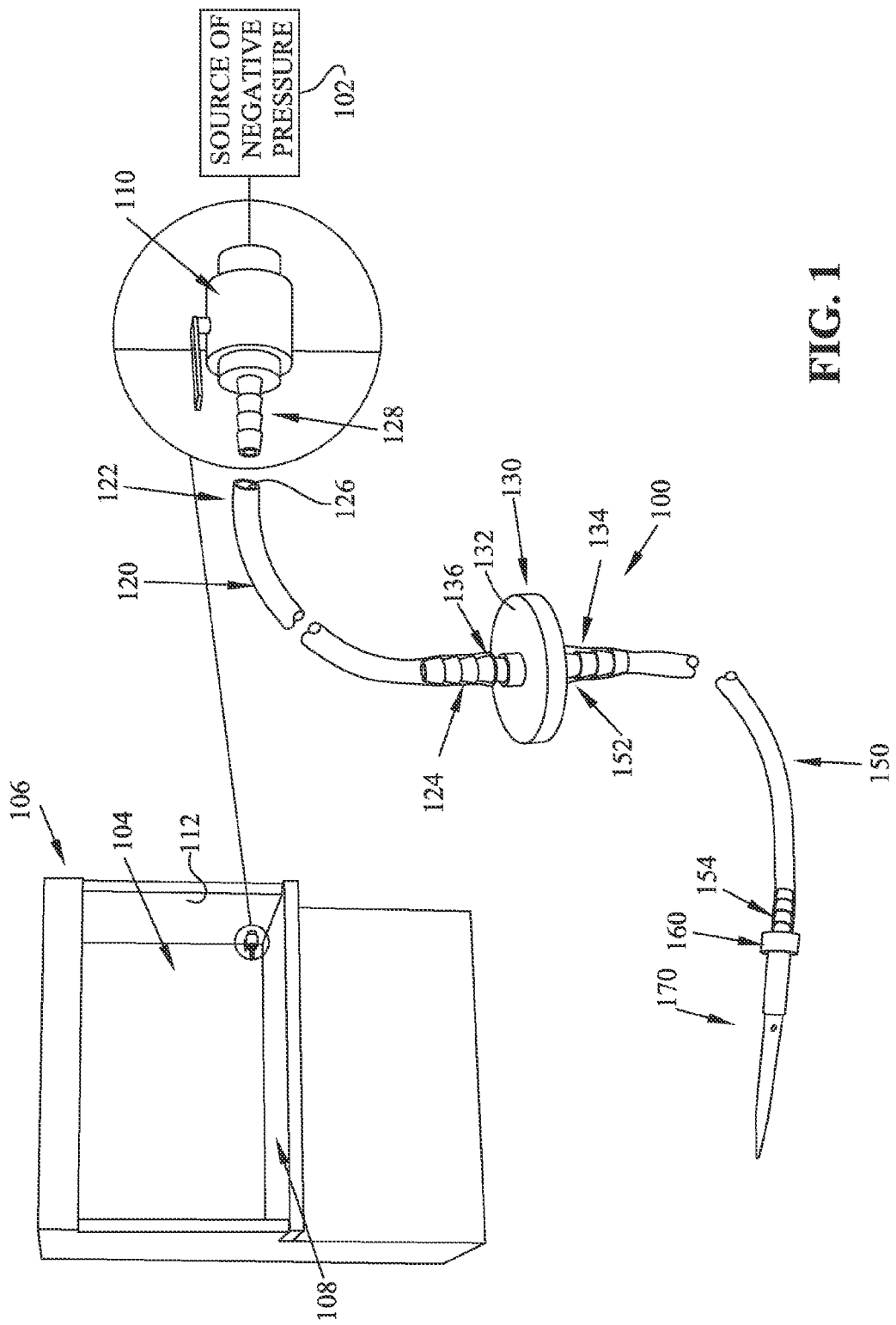
FIG. 1 illustrates a handheld tool for use in transferring plant tissue explants in an aseptic environment.

Referring to FIG. 1, a handheld tool 100 is shown. Handheld tool 100 is used in connection with a source of negative pressure 102 in an aseptic environment 104. In the illustrated embodiment, the aseptic environment 104 is provided in a laminar flow hood 106 having a work surface 108. An exemplary laminar flow hood is the EDGEGUARD® brand laminar flow hood available from The Baker Company located in Sandford, Me. The source of negative pressure 102 is provided to aseptic environment 104 through a valve 110 provided in a sidewall 112 of laminar flow hood 106. An exemplary source of negative pressure 102 is a facility vacuum system. In one embodiment, source of negative pressure 102 has a draw of about 27 inches of mercury below atmospheric pressure.

Figure 2:
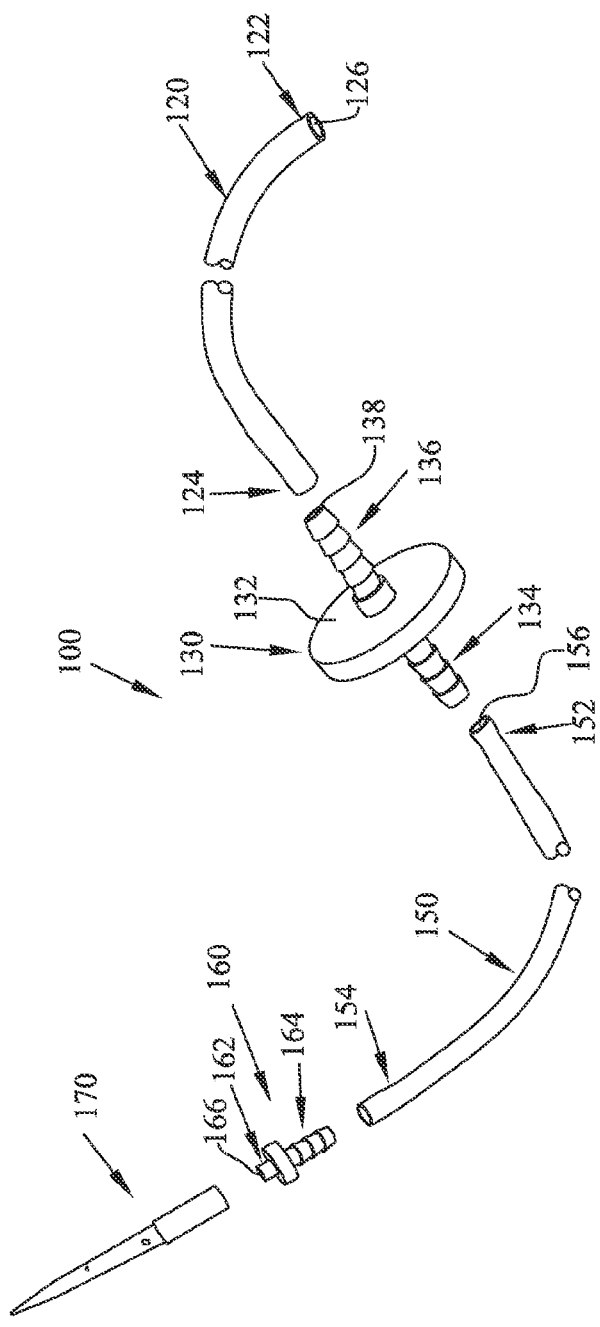
FIG. 2 illustrates a exploded view of the handheld tool of FIG. 1.

Referring to FIG. 2, handheld tool 100 includes a first flexible fluid conduit 120 having a first end 122 and a second end 124. An interior 126 of first flexible fluid conduit 120 is in fluid communication with both first end 122 and second end 124. Returning to FIG. 1, first end 122 is coupled to a hose barb 128 of valve 110. In one embodiment, first flexible fluid conduit 120 is made of a polymeric material. In one embodiment, first flexible fluid conduit 120 is made from an autoclavable material. An exemplary first flexible fluid conduit 120 is 180 PVC non-toxic autoclavable Lab/FDA/USP VI Grace (¼"ID) tubing available from NALGENE Labware having an office at 75 Panorama Creek Drive, Rochester, N.Y. 14625.

Returning to FIG. 2, handheld tool 100 further includes a filter unit 130. Filter unit 130 includes a housing 132 having a filter (not shown) positioned therein and a first hose barb 134 and a second hose barb 136. An interior 138 of filter unit 130 permits fluid to flows through housing 132 from first hose barb 134 to second hose barb 136 or in reverse. Second hose barb 136 is coupled to second end 124 of first flexible fluid conduit 120. An exemplary filter unit 130 is Millipore 50 mm Millex Sterile Filter Unit stepped hose barb with female Luer slip interior available from Millipore having an office at 290 Concord Road, Billerica, Mass. 01821.

Handheld tool 100 further includes a second flexible fluid conduit 150 having a first end 152 and a second end 154. An interior 156 of second flexible fluid conduit 150 is in fluid communication with both first end 152 and second end 154. Returning to FIG. 1, first end 152 is coupled to hose barb 134 of filter unit 130. In one embodiment, second flexible fluid conduit 150 is made of a polymeric material. In one embodiment, first flexible fluid conduit 120 is made from an autoclavable material. An exemplary second flexible fluid conduit 150 is the 180 PVC non-toxic autoclavable Lab/FDA/USP VI Grace (¼"ID) tubing available from NALGENE Labware.

Handheld tool 100 further includes a coupler 160 having a first end 162 and a second end 164. An interior 166 of coupler 160 is in fluid communication with both first end 162 and second end 164. Second end 164 includes a hose barb which is coupled to second end 154 of second flexible fluid conduit 150 as shown in FIG. 1. An exemplary coupler is the Fisher brand Polyethylene Quick Disconnects® 15-315-27D available from Fisher Scientific located at 2000 Park Lane Drive in Pittsburgh, Pa. 15275.

Figure 3:
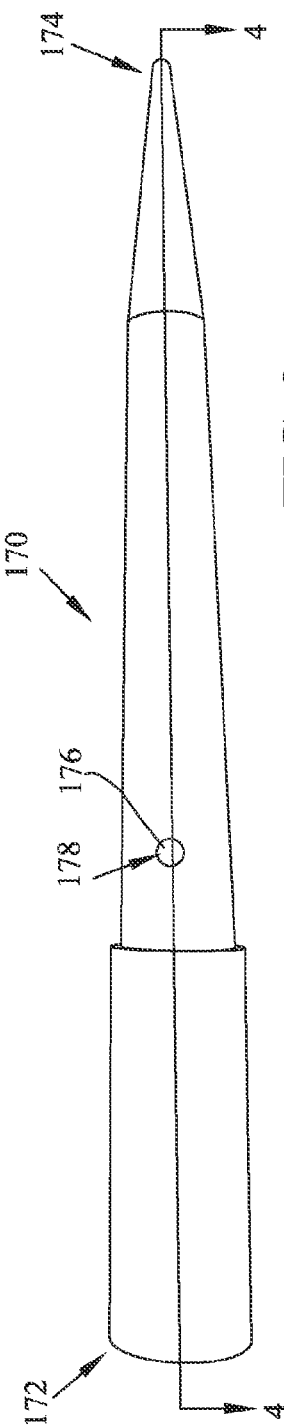
FIG. 3 illustrates a top view of a tip member of the handheld tool of FIG. 1.

Referring to FIG. 3, handheld tool 100 further includes a tip member 170 having a first end 172 and a second end 174. An interior 176 of tip member 170 is in fluid communication with first end 172 and second end 174. Tip member 170 is shown having a generally tapered exterior from first end 172 down to second end 174. Other shapes of tip member 170 may be used. In one embodiment, tip member 170 is a standard pipette tip. An exemplary pipette tip is the LTS 1000 ul wide-bore pipette tip available from Rainin Instrument, LLC, located at 7500 Edgewater Drive, P.O. Box 2160 in Oakland, Calif.

Referring to FIG. 4, interior of tip member 170 includes a first region 180 sized to press-fit with first end 162 of coupler 160. Tip member 170 may be coupled to coupler 160 in other manners as well. Suitable methods for coupling include mating threads and other suitable methods. In one embodiment, interior 176 includes a filter 182 positioned in a region 184.

As shown in FIG. 4, interior of tip member 170 terminates in an opening 186 at second end 174 of tip member 170. Opening 186 is sized to prevent the entrance of a first tissue explant 190A into interior of tip member 170. As explained herein, source of negative pressure 102 draws air in interior 176 generally in direction 192 which results in first tissue explant 190A becoming coupled to second end 174 of tip member 170. Based on the amount of draw of source of negative pressure 102, opening 186 is sized to provide a sufficient surface area to couple first tissue explant 190A to second end 174 of tip member 170. In one embodiment, source of negative pressure 102 draws about 27 inches of mercury below atmospheric pressure and opening 186 is about 40 thousandths of an inch in diameter. Of course different amounts of draw of source of negative pressure 102 and sizes of opening 186 may be used as long as they are sufficient to couple first tissue explant 190A to tip member 170.

As mentioned above, tip member 170 also includes vent passage. As shown in FIG. 4, when vent passage is open to atmosphere air is drawn by source of negative pressure 102 through both vent passage 178 and opening 186. Vent passage 178 is sized such that even if first tissue explant 190A is contacting second end 174 of tip member 170 a sufficient amount of air is provided through vent passage 178 to prevent the coupling of first tissue explant 190A to tip member 170. In one embodiment, vent passage 178 is about 0.08 inches in diameter (area of about 0.02 square inches) while opening 186 is about 0.04 inches in diameter (area of about 0.005 square inches). In one embodiment, the area of vent passage 178 is about four times the area of opening 186. In one embodiment, the area of vent passage 178 is at least about four times the area of opening 186. In one embodiment, the area of vent passage 178 is greater than the area of opening 186.

Figure 5:
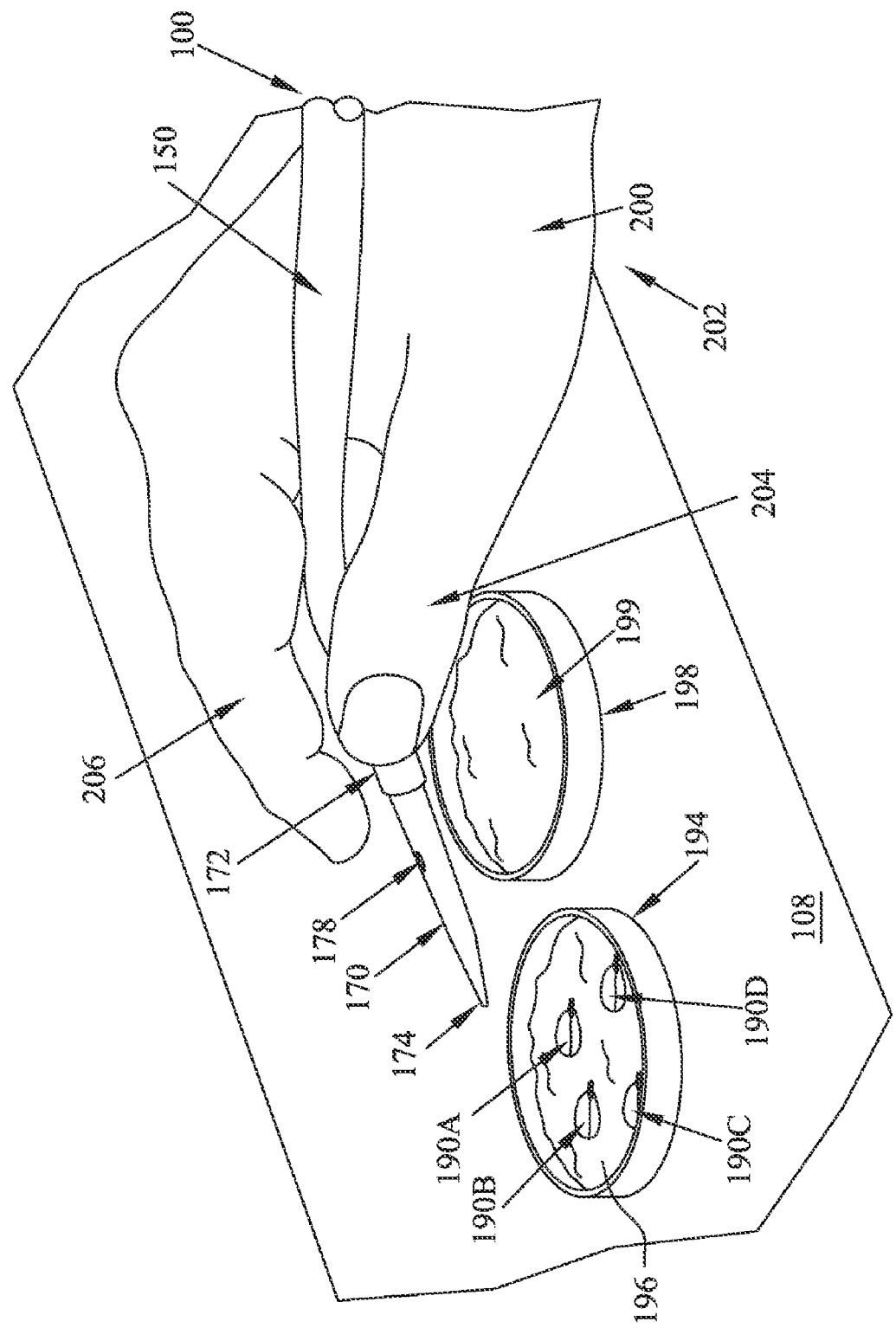
FIG. 5 illustrates an operator using the handheld tool of FIG. 1 to select a first tissue explant in a first container for transfer to a second container.

Referring to FIG. 5, handheld tool 100 is being held in a hand 200 of an operator 202. First end 172 of tip member 170 and coupler 160 (not shown) are being held between a thumb 204 and middle finger (not shown) of operator 202. An index finger 206 of operator 202 is positioned above tip member 170. As explained herein, index finger 206 is positioned such that index finger 206 may cover vent passage 178 during the use of handheld tool 100.

Also shown in FIG. 5 is a first container 194 including a plurality of plant tissue explants 190, four plant tissue explants 190A-D being illustrated. The plurality of plant tissue explants 190 are supported on a nutrient medium 196. Exemplary nutrient mediums include a mixture of inorganic salts, vitamins, a carbon source such as sucrose, and plant growth regulators. Plurality of plant tissue explants 190 are spaced apart in first container 194. Generally first container 194 includes a lid which is placed over a dish of first container 194 when plurality of plant tissue explants 190 are not being transferred. A second container 198 is also shown in FIG. 5 having a nutrient medium 199. The plurality of plant tissue explants 190 are being transferred from first container 194 to second container 198 to provide a fresh nutrient medium 199 for the plurality of plant tissue explants 190.

The use of handheld tool 100 will now be explained with references to FIGS. 4-9. An operator 202 positions first container 194 and second container 198 on work surface 108 of laminar flow hood 106. As such, first container 194 and second container 198 are positioned in an aseptic environment. The operator 202 then grasps handheld tool 100 as shown in FIG. 5 and prepares to transfer plurality of plant tissue explants 190, one at a time, from first container 194 to second container 198. In one embodiment, handheld tool 100 includes multiple tip members so that multiple tissue explants 190 may be coupled at the same time.

It should be noted that if a prior transfer of plant tissue material was just completed with handheld tool 100, a new or cleaned tip member 170 would be first assembled to coupler 160 and the prior tip member 170 would be cleaned or discarded. In one embodiment, tip member 170 is made of an autoclavable material and is cleaned in an autoclave device subsequent to use. The use of a new or cleaned tip member 170 maintains the aseptic environment between transfer runs.

Figure 7:
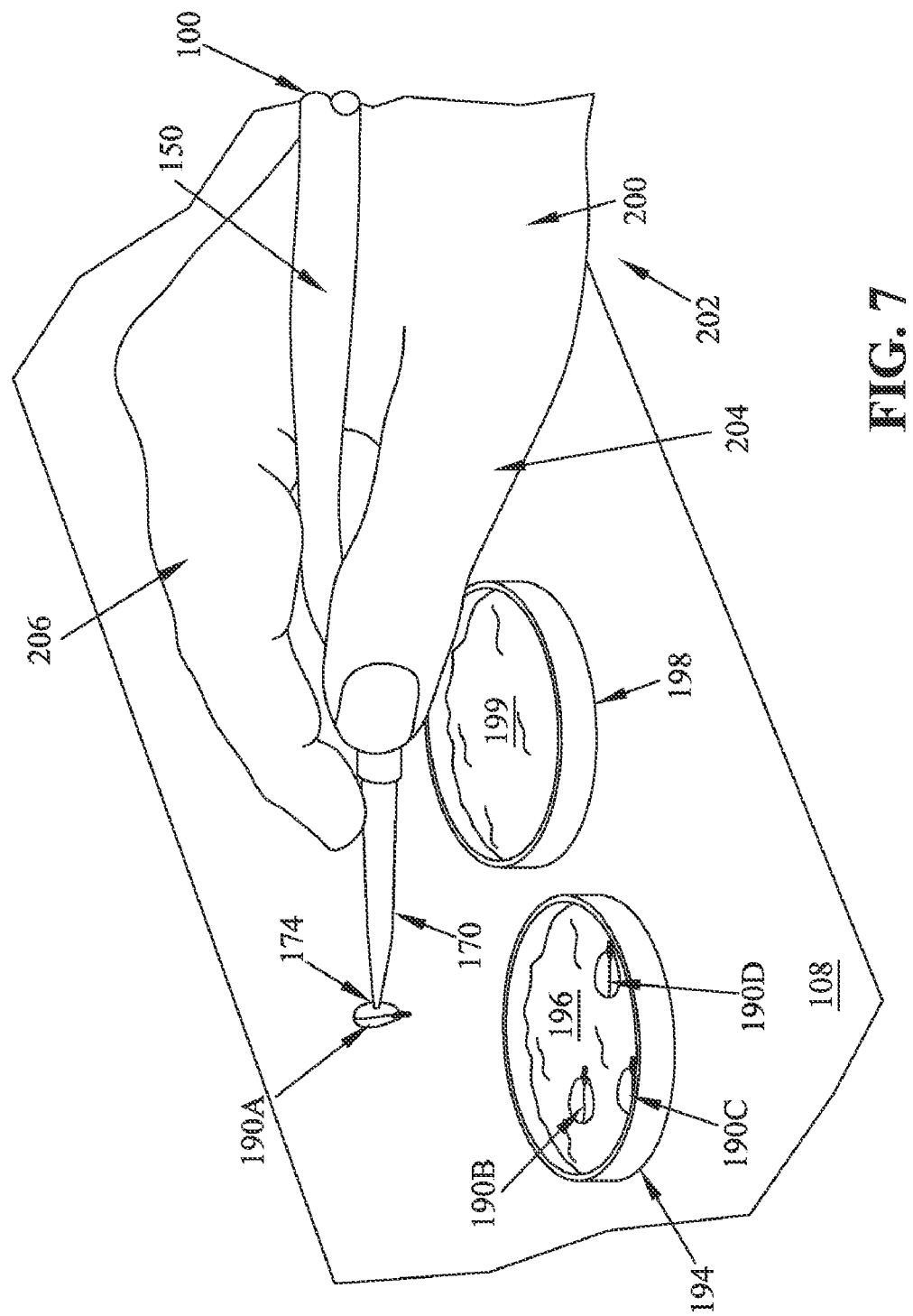
FIG. 7 illustrates the operator using their finger as the stop device such that the first tissue explant is coupled to the end of the tip member and is being transferred to the second container.
Figure 9:
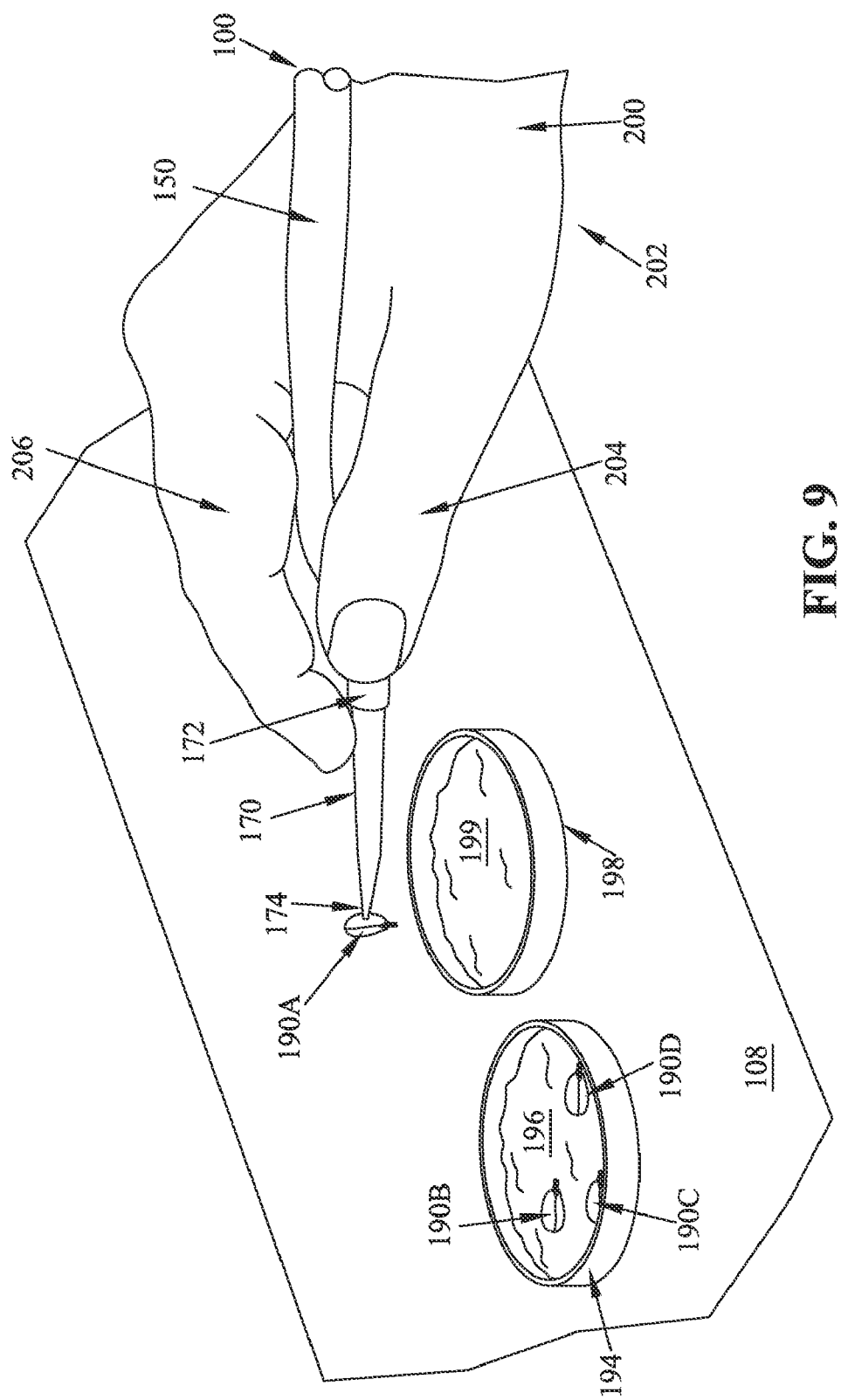
FIG. 9 illustrates the operator having the first tissue explant positioned over the second container.

Referring to FIG. 5, a stop device 210 blocks vent passage 178 from communicating with the atmosphere. As shown in FIG. 4, in the absence of the presence of stop device 210 blocking vent passage 178, air flows into tip member 170 through both vent passage 178 and opening 186 due to the draw of source of negative pressure 102. When stop device 210 blocks vent passage 178 the air flow into tip member 170 through vent passage 178 is greatly reduced or prevented. This results in the air mainly entering tip member 170 through opening 186. As second end 174 of tip member 170 is brought closer to first tissue explant 190A, first tissue explant 190A is coupled to opening 186 due to the draw of source of negative pressure 102, as shown in FIGS. 6 and 7. First tissue explant 190A now moves with tip member 170 such that it may be separated from nutrient medium 196 and moved to second container 198 (see FIG. 9) and placed upon nutrient medium 199. Once placed on nutrient medium 199, first tissue explant 190A is uncoupled from tip member 170 moving stop device 210 to allow more air in through vent passage 178. This reduces the draw experienced by first tissue explant 190A at opening 186 and causes first tissue explant 190A to be released. This process is repeated for each of the plurality of plant tissue explants 190 in first container 194. In one embodiment, operator 202 transfers all of plurality of plant tissue explants 190 from first container 194 to second container 198. In one embodiment, operator 202 transfers only a portion of plurality of plant tissue explants 190 from first container 194 to second container 198 and discards the remainder. In one embodiment, in the early transfer runs (first few items the plurality of plant tissue explants 190 are transferred to a new container) all of plurality of plant tissue explants 190 are transferred to the next container. As time goes on, the operator 202 based on their professional judgment may select less than all of the plurality of plant tissue explants 190 for transfer the next time around.

As shown in FIG. 7, stop device 210 is illustratively index finger 206 of hand 200. (Of course, operator 202 may be wearing gloves or attire which would contact tip member 170.) Thus, an operator 202 may couple first tissue explant 190A by simply lowering index finger 206 to cover vent passage 178 and release first tissue explant 190A by simply raising index finger 206 to be spaced apart from vent passage 178. This repetitive motion is less fatiguing on operator 202 over the course of the day than the use of forceps as described herein. Other types of stop device 210 may be used. In one embodiment, operator 202 may actuate a valve to block and unblock vent passage 178. In one embodiment, operator 202 may cover vent passage 178 with a lid or other type of cover to block vent passage 178 and remove the same to unblock vent passage 178.

As stated above, tip member 170 may be uncoupled from the remainder of handheld tool 100 once a transfer of plurality of plant tissue explants 190 from first container 194 to second container 198 is complete. Tip member 170 is then cleaned or discarded. Another tip member 170 is coupled to the remainder of handheld tool 100 and a subsequent transfer run of other plurality of plant tissue explants 190 is performed.

Referring to FIG. 10, another handheld tool 250 is shown. Handheld tool 250 is identical to handheld tool 100 from coupler 160 back to first flexible fluid conduit 120. Handheld tool 250 also includes a tip member 252 which is identical to tip member 170, except that vent passage 178 is not included. Tip member 252 includes a first end 254 and a second end 256 in fluid communication with the first end 254 through an interior 257 of tip member 252. Tip member 252 includes an opening 258 which operates the same as opening 186.

In one embodiment, tip member 252 is a pipette tip. An exemplary pipette tip is the LTS 1000 ul wide-bore pipette tip available from Rainin Instrument, LLC, located at 7500 Edgewater Drive, P.O. Box 2160 in Oakland, Calif. In the case of tip member 170, in one embodiment, the pipette tip is altered to include vent passage. In contrast, tip member 252 may be an off-the-shelf pipette tip.

Interposed between coupler 160 and tip member 252 is a pen-shaped instrument 262 having a first end 264 and a second end 266. An interior 268 of pen-shaped instrument 262 is in fluid communication with both first end 264 and second end 266. Pen-shaped instrument 262 includes a vent passage 260. Pen-shaped instrument 262 is shown being generally a tapered cylinder. However, pen-shaped instrument 262 may have any suitable shape for comfortable holding by the hand 200 of the operator 202.

Figure 12:
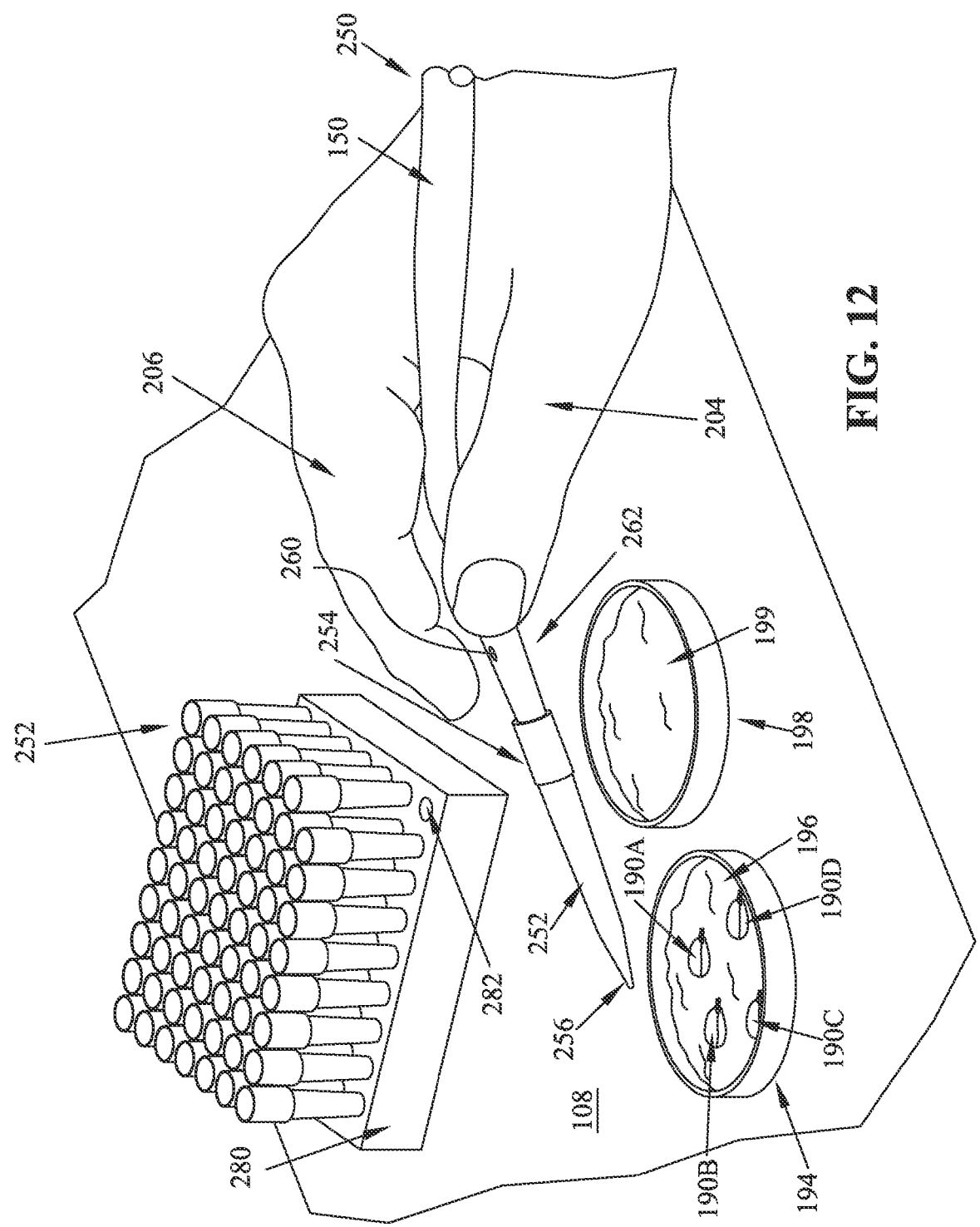
FIG. 12 illustrates the handheld tool of FIG. 10 being used by an operator.

Referring to FIGS. 11 and 12, the operation of handheld tool 250 is explained. An operator 202 positions first container 194 and second container 198 on work surface 108 of laminar flow hood 106. As such, first container 194 and second container 198 are positioned in an aseptic environment. The operator 202 then grasps handheld tool 250 as shown in FIG. 12 and prepares to transfer plurality of plant tissue explants 190, one at a time, from first container 194 to second container 198. It should be noted that if a prior transfer of plant tissue material was just completed with handheld tool 250, a new or cleaned tip member 252 would be first assembled to pen-shaped instrument 262 and the prior tip member 252 would be cleaned or discarded. In one embodiment, tip member 252 is made of an autoclavable material and is cleaned in an autoclave device subsequent to use. The use of a new or cleaned tip member 252 maintains the aseptic environment between transfer runs.

As shown in FIG. 12, a plurality of tip members 252 are stored in a storage container 280. Storage container 280 includes a plurality of recesses 282 into which second end 256 of tip member 252 are placed for storage. Since a different tip member 252 is used for each transfer run and the remainder of handheld tool 250 does not contact the plurality of plant tissue explants 190 of a prior transfer run, an operator 202 may complete several successive transfer runs without the need for cleaning handheld tool 250 between runs while still maintaining an aseptic environment for each run.

To transfer a first tissue explant 190A from first container 194 to second container 198, operator 202 positions second end 256 adjacent to first tissue explant 190A and blocks vent passage 260 of pen-shaped instrument 262 with a stop device 210. As explained herein, in one embodiment, stop device 210 may be index finger 206 of operator 202. Once vent passage 260 is blocked first tissue explant 190A is coupled to second end 256 due to the draw of source of negative pressure 102. First tissue explant 190A now moves with tip member 252 such that it may be separated from nutrient medium 196 and moved to second container 198 and placed upon nutrient medium 199. Once placed on nutrient medium 199, first tissue explant 190A is uncoupled from tip member 252 by moving stop device 210 to allow more air in through vent passage 260 in pen-shaped instrument 262. This reduces the draw experienced by first tissue explant 190A at opening 258 and causes first tissue explant 190A to be released. This process is repeated for each of the plurality of plant tissue explants 190 in first container 194. In one embodiment, operator 202 transfers all of plurality of plant tissue explants 190 from first container 194 to second container 198. In one embodiment, operator 202 transfers only a portion of plurality of plant tissue explants 190 from first container 194 to second container 198 and discards the remainder. In one embodiment, in the early transfer runs (first few instances that the plurality of plant tissue explants 190 are transferred to a new container) all of plurality of plant tissue explants 190 are transferred to the next container. As time goes on, in later transfer runs the operator 202 based on their professional judgment may select less than all of the plurality of plant tissue explants 190 for transfer the next time around.

Figure 13:
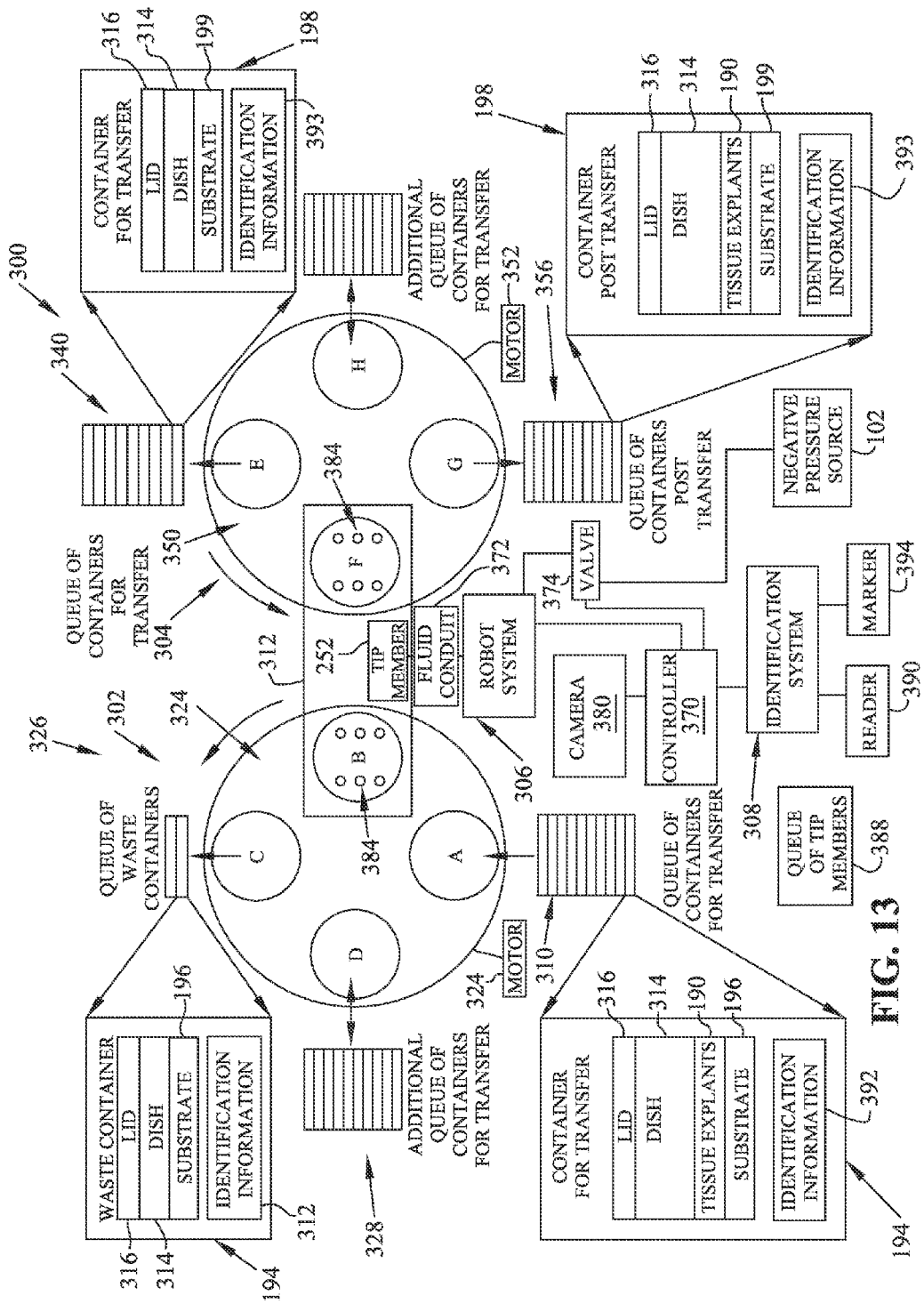
FIG. 13 illustrates a representative view of an automatic transfer system for transferring plant tissue explants from a first container to a second container.

Referring to FIG. 13, a system 300 is illustrated for automatically transferring plant tissue explants from a first container 194 to a second container 198. System 300 performs a transfer run for a plurality of containers in a serial timeframe. In one embodiment, system 300 is housed in a housing which provides an aseptic environment for transferring plant tissue explants.

System 300 includes a first presentment system 302, a second presentment system 304, a robot system 306, and an identification system 308. First presentment system 302 selects a first container 194 from a first queue of containers 310 and moves first container 194 to a region 312. In one embodiment, presentment system 302 also prepares first container 194 so that plurality of plant tissue explants 190 may be accessed by robot system 306. For example, first container 194 may include a dish 314 supporting nutrient medium 196 and plurality of plant tissue explants 190 and a lid 316 covering dish 314. First presentment system 302, in this example, separates lid 316 from dish 314 so that robot system 306 may access plurality of plant tissue explants 190. In one embodiment, first presentment system 302 lowers dish 314 relative to lid 316 to gain access to the plurality of plant tissue explants 190.

In one embodiment, first presentment system 302 includes a turntable 324 which is moved by a motor 314. Turntable 324 of first presentment system 302 supports first container 194 which is removed from queue of containers 310 and moves it to region 312 wherein robot system 306 interacts with plurality of plant tissue explants 190 and then turntable 324 moves it to a second queue 326 of containers. An exemplary system for selecting a container from a vertical queue of containers, moving that container to a region for processing (filling with agar), and then moving the container to a second vertical queue of containers is disclosed in U.S. Pat. No. 4,170,861, the disclosure of which is expressly incorporated by reference herein. Another exemplary system is MEDIAJET petri dish filler available from INTEGRA Biosciences AG of Schönbühlstr. 8, CH-7000 Chur Switzerland. First presentment system 302, in one embodiment, also supports additional queues 328 of containers which may be processed once queue of containers 310 is completed. As shown in FIG. 13, turntable 324 includes a plurality of holders A-D for interacting with a container. As illustrated, holder A removes a container from queue 310. Holder B is for presenting an opened container to robot system 306. Holder C is for placing the container in queue 326. Holder D removes a container from queue 328 once queue 310 is exhausted.

Second presentment system 304 is generally identical to first presentment system 302. Second presentment system 304 selects a second container 198 from a queue of containers 340 and moves second container 198 to region 312. In one embodiment, presentment system 304 also prepares second container 198 so that plurality of plant tissue explants 190 may be placed within second container 198 by robot system 306. For example, second container 198 may include a dish 314 supporting nutrient medium 199 and plurality of plant tissue explants 190 (once transferred by robot system 306) and a lid 316 covering dish 314. Second presentment system 304, in this example, separates lid 316 from dish 314 so that robot system 306 may place plurality of plant tissue explants 190 within second container 198. In one embodiment, second presentment system 304 lowers dish 314 relative to lid 316.

In one embodiment, second presentment system 304 includes a turntable 350 which is moved by a motor 352. Turntable 350 of second presentment system 304 supports second container 198 received from queue of containers 340 and moves it to region 312 wherein robot system 306 places plurality of plant tissue explants 190 within second container 198 and then moves it to a second queue 356 of containers. The containers in second queue 356 are held until removed by an operator for return to the environment designed for the maturing of plurality of plant tissue explants 190. As mentioned above, an exemplary system for selecting a container from a vertical queue of containers, moving that container to a region for processing (filling with agar), and then moving the container to a second vertical queue of containers is disclosed in U.S. Pat. No. 4,170,861, the disclosure of which is expressly incorporated by reference herein. Second presentment system 304, in one embodiment, also supports additional queues 328 of containers which may be processed once queue of containers 310 is completed. As shown in FIG. 13, turntable 350 includes a plurality of holders E-H for interacting with a container. As illustrated, holder E removes a container from queue 340. Holder F is for presenting an opened container to robot system 306. Holder G is for placing the container in queue 356. Holder H removes a container from an additional queue once queue 340 is exhausted.

Robot system 306 may be any sort of robot system capable of moving a tip member 252 into proximity of plurality of plant tissue explants 190 in first container 194 and then moving the plurality of plant tissue explants 190 to second container 198. One exemplary robot system includes an articulated arm. Robot system 306 is controlled by a controller 370 which executes software instructions stored on a computer readable medium to perform the operations of robot system 306. Robot system 306 supports a fluid conduit 372 which is coupled to source of negative pressure 102 through a valve 374. Valve 374 is operatively coupled to controller 370 which opens valve 374 when a respective plurality of plant tissue explants 190 is to be coupled to tip member 252 and closes valve 374 when the respective plurality of plant tissue explants 190 is to be separated from tip member 252. In one embodiment, valve 374 couples and uncouples tip member 252 to/from source of negative pressure 102. In one embodiment, valve 374 opens and closes a vent passage which effectively increases and decreases, respectively, the amount of draw source of negative pressure 102 has at tip member 252.

Robot system 306 includes at least one camera 380 which monitors region 312. Based on the images captured by at least one camera 380, controller 370 is able to guide the movement of tip member 252. In one embodiment, plurality of plant tissue explants 190 are arranged in a predefined arrangement 384 (illustratively two rows of three in FIG. 13) in first container 194 when presented in region 312. Controller 370 moves tip member 252 so that the plurality of plant tissue explants 190 maintain this same predefined arrangement 384 in second container 198). Once all of the plurality of plant tissue explants 190 have been transferred from first container 194 to second container 198, controller 370 moves robot system 306 to place tip member 252 in a waste receptacle or to be cleaned receptacle and couples a sterile tip member 252 to fluid conduit 372 from a queue of tip member 252, represented by 388.

Controller 370 is further operatively coupled to identification system 308. Identification system 308 includes a reader 390 which identifies first container 194 to controller 370. In one embodiment, first container 194 includes identifying indicia on dish 314 or lid 316 of first container 194 and reader 390 reads the indicia. In one example, the indicia includes a bar code and reader 390 reads the bar code and provides this information to controller 370.

Identification system 308 also includes a marker unit 394 which places indicia 393 on at least on one of dish 314 and lid 316 of second container 198. In one embodiment, controller 370 instructs marker unit 394 as to what indicia to place on second container 198. In one example, the indicia includes a bar code. An exemplary system for placing identifying information on second container 198 is disclosed in U.S. Pat. No. 4,572,067, the disclosure of which is expressly incorporated by reference herein.

Referring to FIG. 14, a method 400 of transferring plant tissue explants is provided. In one embodiment, method 400 is performed with system 300. A region is monitored with at least one camera, as represented by block 402. A first container with a plurality of plant tissue explants supported on a first nutrient substrate for transfer is provided in the monitored region, as represented by block 404. In one embodiment, the first container is automatically provided in the monitored region with a presentment system.

In one embodiment, the presentment system includes a robot arm which retrieves the first container and places it in the monitored region. Referring to FIG. 15, in one embodiment, the presentment system performs the method 420 wherein the presentment system identifies the first container, as represented by block 422. In one embodiment, the presentment system includes a reader which provides input to a controller of markings or other indicia associated with first container 194. The presentment system also selects first container 194 from a queue of containers, as represented by block 424. The presentment system further removes a lid of first container 194, as represented by block 426, and moves first container 194 to the monitored region, as represented by block 428.

Returning to FIG. 14, a second container is provided in the monitored region for receiving the plurality of plant tissue explants and supporting the plurality of plant tissue explants on a second nutrient substrate, as represented by block 406. In one embodiment, the second container is automatically provided in the monitored region with a presentment system.

In one embodiment, the presentment system includes a robot arm which retrieves the second container and places it in the monitored region. In one embodiment, the presentment system includes a robot arm which retrieves the second container and places it in the monitored region. Referring to FIG.

16, in one embodiment, the presentment system performs the method 430 wherein the presentment system selects second container 198 from a queue of containers, as represented by block 432, and identifies the second container 198, as represented by block 434. In one embodiment, the presentment system includes a marker which based on input from a controller provides markings or other indicia on second container 198. The presentment system further removes a lid of second container 198, as represented by block 436, and moves second container 198 to the monitored region, as represented by block 438.

Returning to FIG. 14, the plant tissue explants are automatically transferred from the first container to the second container through negative pressure applied by a robot system, as represented by block 408. Once the plurality of plant tissue explants 190 have been transferred first container 194 may be discarded.

Figure 17:
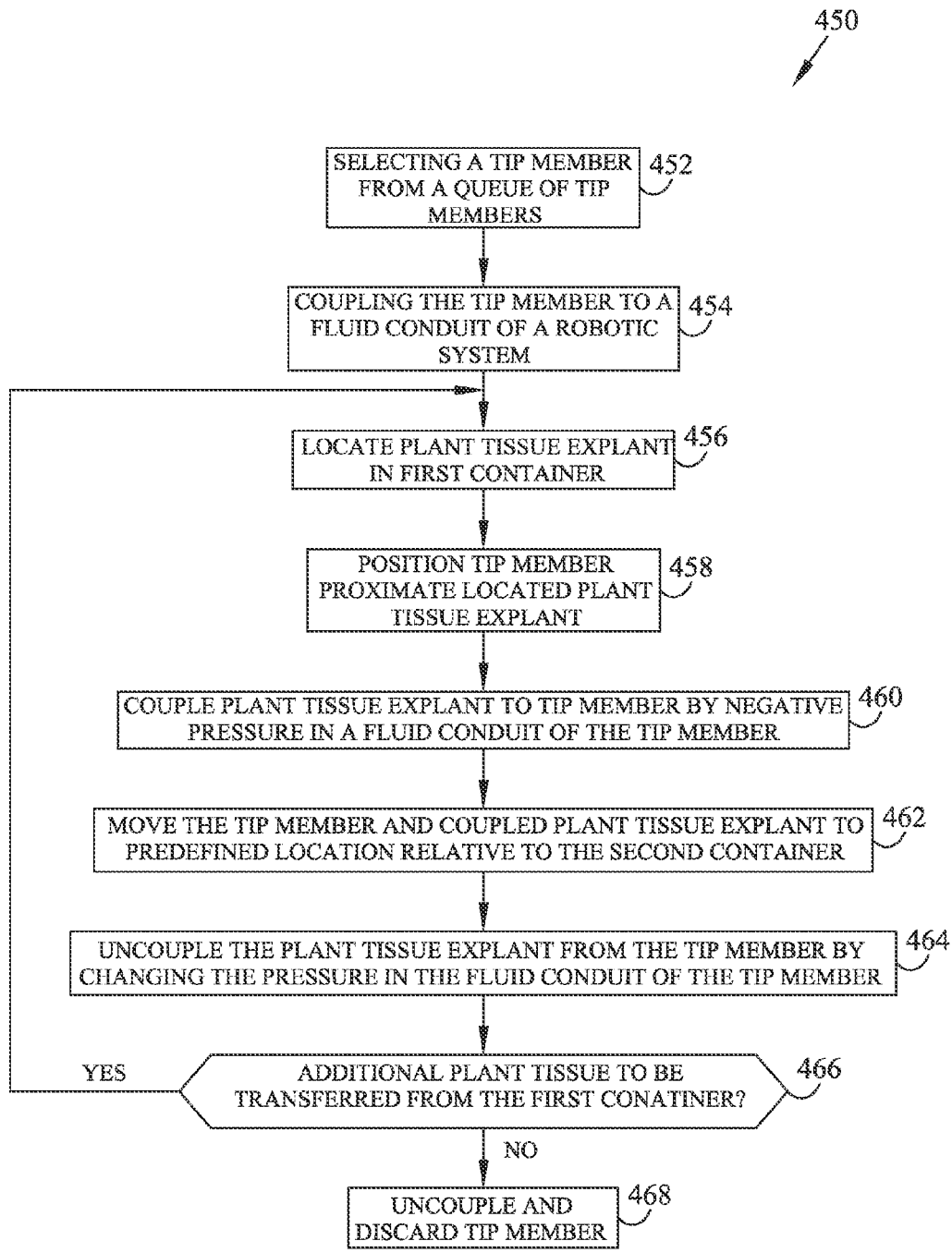
FIG. 17 illustrates a representative method of automatically transferring the plant tissue explants from the first container to the second container.

In one embodiment, the robot system includes a fluid conduit in fluid communication with a source of negative pressure. Referring to FIG. 17, in one embodiment the automatic transfer of the plant tissue explants from the first container to the second container through negative pressure applied by a robot system is performed by method 450. The robot system selects a tip member from a queue of tip members, as represented by block 452. The robot system is coupled the tip member such that a first end of the tip member is in fluid communication with the fluid conduit, as represented by block 454. Once the tip member is in place, the robot system transfers the plant tissue explants from first container 194 to second container 198. For each plant tissue explant in the first container, the robot system locates the respective plant tissue explant in the first container, as represented by block 456 and positions the first end of the tip member proximate the respective plant tissue explant, as represented by block 458. Further, the robot system couples the respective plant tissue explant to the first end of the tip member, as represented by block 460. The respective plant tissue explant is coupled due to the first end of the tip member being in fluid communication with the source of negative pressure through a fluid conduit of the tip member. The robot system then moves the tip member and the respective plant tissue explant to a predefined location relative to the second container, as represented by block 462 and uncouples the respective plant tissue explant from the tip member by changing the pressure in the fluid conduit of the tip member, as represented by block 464. In one embodiment, the pressure in the fluid conduit of the tip member is changed by blocking access to or lessening the draw of source of negative pressure 102. In one embodiment, the pressure in the fluid conduit of the tip member is changed by unblocking a vent passage in the fluid conduit of the robot system. Once the transfer from first container 194 to second container 198 is complete for all of the plurality of plant tissue explants 190 in first container 194 then the tip member is uncoupled from the fluid conduit of the robot system and discarded, as represented by block 468.

While this invention has been described as relative to exemplary designs, the present invention may be further modified within the spirit and scope of this disclosure. Further, this application is intended to cover such departures from the present disclosure as come within known or customary practice in the art to which this invention pertains.

The invention claimed is:

1. A method of transferring plant tissue explants from a first container having a first nutrient medium substrate adapted to provide nutrients to the plant tissue explants to a second container having a second nutrient medium substrate adapted to provide nutrients to the plant tissue explants, the method comprising the steps of:
 (a) coupling a first plant tissue explant to a handheld tool, the handheld tool coupling the first plant tissue explant through a negative pressure present in an interior of the handheld tool;
 (b) generally separating the first plant tissue explant from the first nutrient medium substrate adapted to provide nutrients to the first plant tissue explant and from the first container;
 (c) locating the first plant tissue explant relative to the second nutrient medium substrate adapted to provide nutrients to the first plant tissue explant of the second container; and
 (d) uncoupling the first plant tissue explant from the handheld tool.

2. The method of claim 1, wherein the handheld tool includes a fluid conduit having a first end and a second end, the second end of the fluid conduit being in fluid communication with the first end of the fluid conduit and the fluid conduit having at least one vent passage positioned between the first end of the fluid conduit and the second end of the fluid conduit and being in fluid communication with the first end of the fluid conduit and the second end of the fluid conduit and to the surrounding environment, the vent passage being blocked from fluid communication with the surrounding environment during steps (a) through (c) with a stop device and the vent passage being in fluid communication with the surrounding environment during step (d).

3. The method of claim 2, wherein stop device is one of an operator's finger and a device supported by the operator's finger.

4. The method of claim 2, wherein the fluid conduit is an assembly and includes at least a first portion and a second portion, both the first portion and the second portion having a respective interior in fluid communication with the first end of the handheld tool and the second end of the handheld tool when the first portion and the second portion are assembled, the method further comprising the steps of:
 (e) providing a plurality of first portions of the handheld tool;
 (f) assembling a first one of the plurality of first portions of the handheld tool to the second portion of the handheld tool;
 (g) performing steps (a) through (d) for all of the plant tissue explants in the first container selected for transfer to the second container;
 (h) separating the first one of the plurality of first portions of the handheld tool from the second portion of the handheld tool;
 (i) obtaining a third container including another plurality of plant tissue explants for transfer to a fourth container;
 (j) assembling a second one of the plurality of first portions of the handheld tool to the second portion of the handheld tool; and
 (k) performing steps (a) through (d) for all of the plant tissue explants in the third container selected for transfer to the fourth container.

5. The method of claim 4, wherein the plurality of first portions are a plurality of pipette tips.

6. The method of claim 5, wherein the plurality of pipette tips are stored generally vertical in a pipette tip box with a tip portion lower than a coupling portion, the step of assembling a first one of the plurality of first portions of the handheld tool to the second portion of the handheld tool includes the step inserting a portion of the second portion of the handheld tool into the coupling portion of a first pipette tip of the plurality of pipette tips while the first pipette tip is stored in the pipette tip box.

7. The method of claim 1, wherein steps (a) through (d) are performed in an aseptic environment.

8. The method of claim 7, wherein steps (a) through (d) are performed in a laminar flow hood.

9. The method of claim 1, wherein the step of uncoupling the first plant tissue explant from the handheld tool includes the step of reducing the negative pressure in the handheld tool by opening a vent passage of the handheld tool.

10. The method of claim 1, further comprising the step of preventing the first plant tissue explant from entering into an interior of the handheld tool.

11. The method of claim 10, wherein the first plant tissue explant is coupled to a first end of the handheld tool, the first end of the handheld tool including an opening sized to prevent the first plant tissue explant from entering into the interior of the handheld tool.

12. The method of claim 1, wherein during step (c) the first plant tissue explant is held stationary relative to the handheld tool.

13. The method of claim 2, further comprising the step of filtering the fluid as it travels between the first end of the fluid conduit and the second end of the fluid conduit.

* * * * *